United States Patent [19]
LaClair

[11] Patent Number: 5,675,249
[45] Date of Patent: Oct. 7, 1997

[54] PORTABLE OPTICAL FLUID DEBRIS DETECTOR INCLUDING COVER AND CALIBRATING MAGNET

[75] Inventor: Robert Downing LaClair, Richmond, Vt.

[73] Assignee: Simmonds Precision Products, Inc., Richfield, Ohio

[21] Appl. No.: 209,575

[22] Filed: Mar. 10, 1994

[51] Int. Cl.$^6$ .......................... G01N 27/74; G01N 35/02; G01J 4/02
[52] U.S. Cl. ...................... 324/204; 250/227.17; 324/202
[58] Field of Search ................... 324/244.1, 204, 324/262, 173, 174; 340/631; 250/227.17; 73/53.05, 10

[56] References Cited

U.S. PATENT DOCUMENTS

| | | | |
|---|---|---|---|
| 2,462,715 | 2/1949 | Booth | 324/244.1 |
| 3,404,337 | 10/1968 | Pool et al. | 340/631 |
| 4,219,805 | 8/1980 | Magee et al. | 340/631 |
| 4,323,843 | 4/1982 | Batham | 324/204 |
| 4,518,857 | 5/1985 | McMahon et al. | 250/225 |
| 4,554,449 | 11/1985 | Taniuchi et al. | 250/227 |
| 4,831,362 | 5/1989 | Tsaprazis | 340/515 |
| 4,843,232 | 6/1989 | Emo et al. | 250/225 |
| 4,947,035 | 8/1990 | Zook et al. | 250/225 |
| 5,038,102 | 8/1991 | Glasheen | 324/175 |
| 5,070,298 | 12/1991 | Honda et al. | 324/207.25 |
| 5,149,962 | 9/1992 | Maurice | 250/227.17 |
| 5,179,346 | 1/1993 | McGee et al. | 324/204 X |
| 5,214,377 | 5/1993 | Maurice et al. | 324/204 |
| 5,264,832 | 11/1993 | Parmer | 324/204 |
| 5,334,831 | 8/1994 | Maurice | 250/227.17 |
| 5,334,932 | 8/1994 | Nielsen | 324/204 |

FOREIGN PATENT DOCUMENTS

| | | |
|---|---|---|
| 9015613 | 3/1991 | Germany. |
| 62-90547 | 4/1987 | Japan. |
| 62-76474 | 4/1987 | Japan. |
| 2029580 | 3/1980 | United Kingdom. |

OTHER PUBLICATIONS

Maurice et al., "Los cost binary proximity sensor for automotive applications," SPIE vol. 1173 Fiber Optic Systems For Mobile Platforms III (1989), pp. 75–83.

QDM (Quantitative Debris Monitoring) System, "Oil Debris Monitoring System Comparisons," Aeroquip Corporation, 1988.

Society of Automotive Engineers, Inc., Aerospace Information Report, Issued Mar. 1, 1984, AIR 1828.

*Primary Examiner*—Sandra L. O'Shea
*Assistant Examiner*—Roger C. Phillips
*Attorney, Agent, or Firm*—Richard A. Romanchik; Leonard L. Lewis

[57] ABSTRACT

Apparatus for detecting ferromagnetic debris in a fluid medium in a container includes a plug attachable to the container and having an associated magnetic field preferably produced by a permanent magnet. The plug is at least partly exposed to the fluid to capture debris in the fluid. The apparatus further includes a portable sensor for optically sensing the captured debris, with the sensor having a probe that is connectable to the plug. A method for using such apparatus is provided, and in general a method of detecting ferromagnetic particles in a fluid medium in a container includes the steps of: a) magnetically capturing particles from the fluid using a plug with the container, and b) interrogating the plug with light for captured particles using a portable probe.

6 Claims, 3 Drawing Sheets

5,675,249

PORTABLE OPTICAL FLUID DEBRIS DETECTOR INCLUDING COVER AND CALIBRATING MAGNET

BACKGROUND OF THE INVENTION

The invention relates generally to detecting various characteristics of debris entrained in a fluid medium. Such characteristics can include quantity of particles, total mass and rate of accumulation. More specifically, the invention relates to detecting ferrous or ferromagnetic debris in a lubricating fluid such as engine oil. The invention is particularly useful in detecting debris in aircraft engine oil.

It has been discovered recently that electromagnetic energy can be used in an optical detector to detect ferromagnetic debris in a fluid medium as disclosed in U. S. Pat. No. 5,214,377 issued May 25, 1993 to Maurice et al. and commonly owned by the assignee of the instant invention. Such an optical detector utilizes a magnetic field probe to capture debris in the fluid and using a magneto-optic sensor to modulate light energy in response to changes in the magnetic field caused by accumulation of debris on the probe. An important advantage of the optical detector is that it is relatively immune to electromagnetic interference at the sensor. The optical detector is also nonintrusive and only uses light energy within the sensor itself.

One of the many uses for such an optical sensor disclosed in the aforementioned patent application is in connection with aircraft engine maintenance. The optical detector can conveniently be used with on-board electronics to provide a real-time monitor of the oil and engine performance. Just as frequently, however, engine maintenance and monitoring is preformed by ground crews and technicians. In many situations it would be advantageous to have a portable and simple-to-use optical debris monitor that could be used on many aircraft and at anytime that aircraft are available to the ground crews. Such a debris monitor should, if desired, be usable in close proximity to an aircraft engine without applying electrical energy such as voltage or current near the engine or fuel tanks.

SUMMARY OF THE INVENTION

The instant invention provides, in one embodiment, apparatus for detecting ferromagnetic debris in a fluid medium in a container, such apparatus comprising a plug attachable to the container and having an associated magnetic field, the plug being disposed near the fluid to capture debris in the fluid. Such apparatus further comprises a portable sensor for optically sensing the captured debris, with the sensor having a probe that is connectable to the plug. The invention also contemplates a method for using such apparatus, and in general a method of detecting ferromagnetic particles in a fluid medium in a container comprising the steps of: a) magnetically capturing particles from the fluid using a plug with the container, and b) interrogating the plug with light for captured particles using a portable probe.

These and other aspects and advantages of the present invention will be apparent to any person skilled in the art from the following detailed description of the preferred embodiment of the invention including the best mode contemplated for carrying out my invention.

DESCRIPTION OF THE PREFERRED EMBODIMENT

Figure 1:
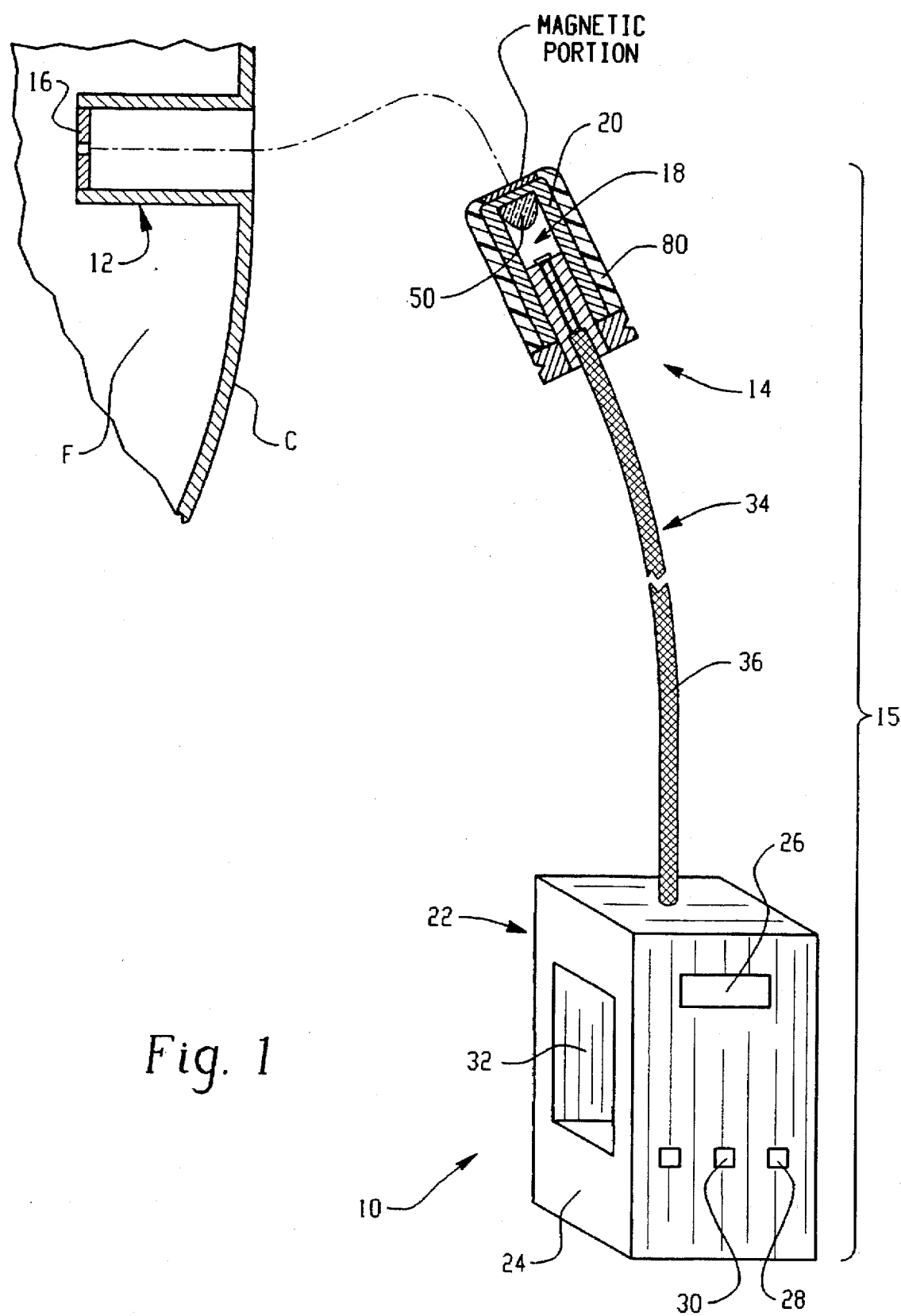
FIG. 1 is a simplified schematic diagram of a portable debris monitor according to the invention.

With reference to FIG. 1, a portable debris monitor according to the present invention is indicated generally by the numeral 10. In the preferred embodiment, the monitor 10 includes a plug type assembly 12 that is attachable to or formed integral with a container "C" for a fluid medium "F" such as, for example, lubricating oil and a portable sensor 15. A typical example of the plug 12 would be an oil plug for an aircraft engine such as, for example, a jet turbine engine. Although the invention is described herein by way of example and reference to detecting ferromagnetic particles and debris in aircraft engine oil, this is for purposes of explanation only and should not be construed in a limiting sense. Anyone skilled in the art will readily appreciate that all the advantages and aspects of the invention can be realized for use with any fluid medium, liquid or gaseous, having entrained ferromagnetic particles that can be captured by a magnetic field. Also, the use with respect to an aircraft engine is but one of any number of environments wherein the benefits and improvements of the invention can be realized. Therefore, as used herein, the terms "fluid" and "container" should be construed in their broadest sense.

The plug 12 preferably is mounted on the container C by any convenient means (not shown). In many aircraft applications, the plug is designed as a removable device to permit analysis and/or replacement. The invention as described herein contemplates that preferably the plug 12 and a probe assembly 14 be manually connectable or mateable together. This can be accomplished by connecting the two while the plug is with the container, or can be done after the plug has been removed from the container. In either situation, the plug 12 contains captured debris and can be interrogated by the probe 14.

Figure 2:
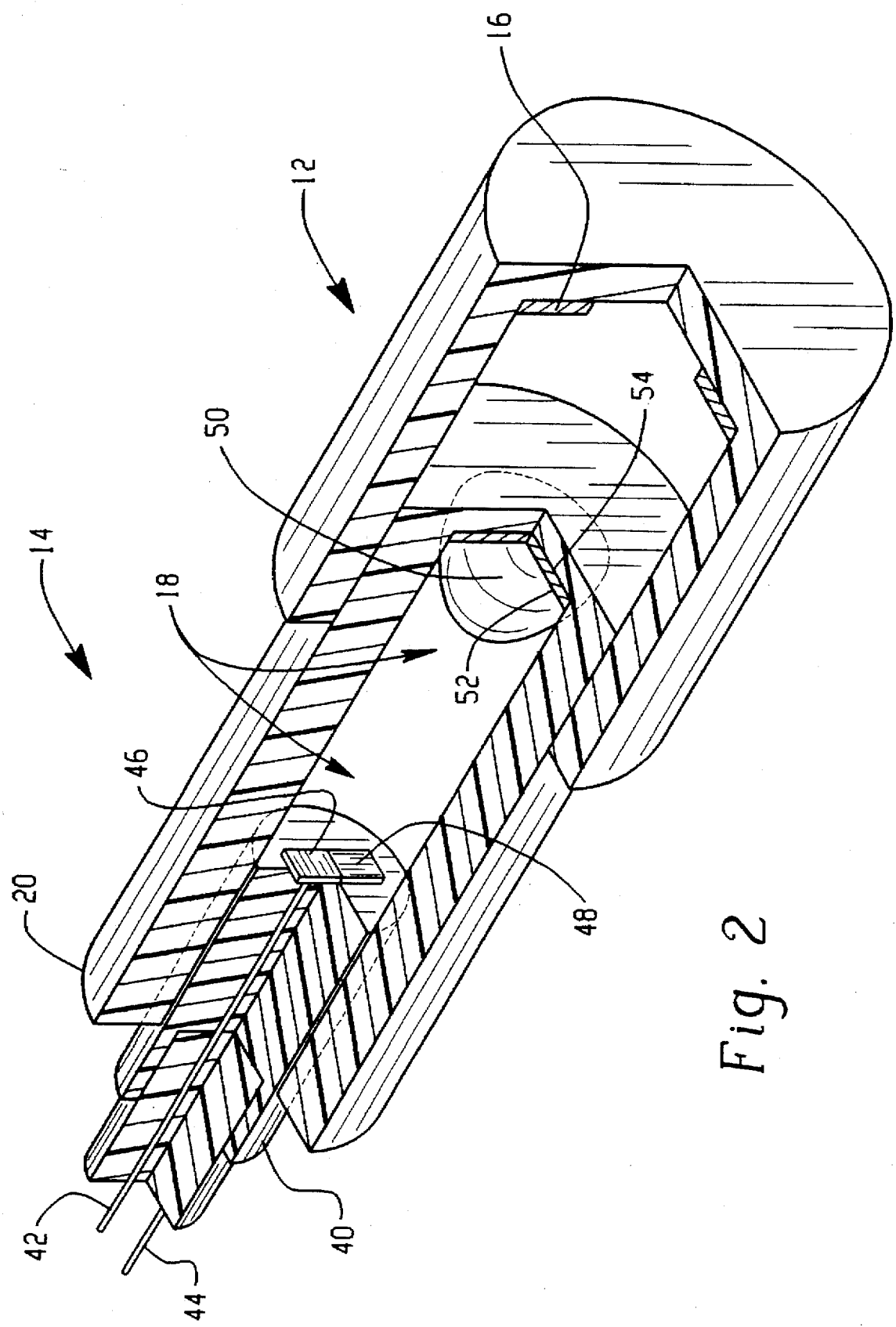
FIG. 2 is a more detailed schematic of a plug and probe design useful with the present invention.

The plug 12 is conveniently formed as a female receptacle and includes a permanent magnet such as a ring magnet 16. The plug 12 is designed so as to slidably receive a magneto-optic sensor 18 that is part of the probe assembly 14. As best shown in FIG. 2, the probe 14 includes a cylindrical casing 20 that retains the magneto-optic sensor and that can be easily inserted into and removed from the plug assembly 12 as a complete unit.

Referring again to FIG. 1, the debris monitor 10 includes the portable sensor 15 that further includes an electro-optic transducer 22 that can conveniently be self-contained in a lightweight portable and preferably hand-held housing 24. The transducer 22 may be provided with any number of useful data readout devices and controls such as a visual display 26, a calibrate/sense switch 28 and an ON/OFF power switch 30. The housing 24 may also be provided with a recess or storage cavity 32 to stow the probe assembly 14 during nonuse or while transporting the transducer and probe unit.

An optic fiber cable 34 is connectable at one end to an input of the probe assembly 14 and at an opposite end to the transducer assembly 22. The fibers can be terminated for use by any conveniently available means such as optical contacts and connectors. In the preferred embodiment, the cable 34 includes two optic fibers each of which may be enclosed within a protective reinforcing member such as a plastic sleeve (not shown). The fibers can then be further protected by a reinforced harness such as a nylon mesh 36. Other reinforcing members could be used depending on whether the user wants a flexible cable or a more rigid cable.

An important aspect of the invention is that preferably the probe assembly 14 only contains nonelectrical optics and operates with electromagnetic energy. Thus, no voltage or current is present in the probe which is a significant safety improvement when the probe is inserted into to plug assembly.

The design, configuration and operation of the probe assembly 14 optics and the transducer assembly 22 electronics are completely described in the aforementioned U.S. Pat. No. 5,214,377, the entire disclosure of which is fully incorporated herein by reference. Only a brief summary of that disclosure will be repeated herein to explain how such a debris monitor can be used with the present invention.

Referring now to FIG. 2, the probe assembly 14 includes the casing 20 that slidably receives a ferrule 40 that holds the respective terminal ends of optic fibers 42, 44. The first optic fiber 42 abuts a first polarizer 46 and the second optic fiber 44 abuts a second polarizer 48. In the preferred embodiment the polarizers are oriented at forty-five degrees with respect to each other, thus providing an optical path for light transmitted bidirectionally through the fibers 42,44.

A lens 50 can be provided for collimating the polarized light. The lens 50 focuses the light for transmission through a magneto-optic material 52 such as, for example, a Faraday film or glass. The magneto-optic element 52 preferably includes a light reflective or mirrored back surface 54 such that the optic fibers 42,44, the optional lens 50, the magneto-optic element 52 and the reflective surface 54 define a folded optical path for light entering the probe assembly 14 via the fibers 42,44. The probe assembly 14 can also be realized with an unfolded optical path but this is less preferred due to the substantial size reduction in the probe using the folded optical path.

As further illustrated in FIG. 2, the plug assembly 12 is arranged to slidably receive the probe so that when the probe is properly inserted the magneto-optic element 52 is positioned in a predetermined manner with respect to the magnet 16. As explained in greater detail in the referenced patent, the magneto-optic material 52 is positioned so that a portion of the magnetic field is aligned generally parallel to the axis of light propagation through the magneto-optic material. Accumulation of ferromagnetic debris on the plug causes the magnetic flux through the magneto-optic material to change and these changes can be detected by corresponding changes in the polarization angle of light transmitted through the magneto-optic material 52.

In operation, light is transmitted bidirectionally through the optic fibers from the electro-optic transducer 22. During one cycle, light passes from one of the fibers through its respective polarizer, then through the lens and the magneto-optic material. The light is then reflected back through the magneto-optic material into the lens and then into the other fiber for transmission back to the electro-optic transducer 22. In the succeeding transmission, light enters the probe through the fiber that was last used as the output fiber, travels along the optical path and exits through the other fiber that now serves as the output fiber. The use of bidirectional transmission permits self-referencing of the light signal and a built-in-test capability. When the folded optical path is used the light passes through the magneto-optic material twice during each transmission. As is well-known, the Faraday effect is such that the polarization rotation does not depend on the direction of the light propagation through the magneto-optic material, thus producing twice the polarization rotation when the folded optical path is used.

An important advantage of the bidirectional transmission is the use of self-referencing. The debris monitor 10 detects the small changes in the magnetic field caused by accumulation of debris on the plug 12 because the changing magnetic field will cause a modulation of the polarization angle of light transmitted through the magneto-optic material. The use of a second polarizer as an analyzer with each transmission of interrogating light provides a means for detecting the polarization rotation because the intensity of the light exiting the analyzer corresponds to the magnetic field characteristic and thus the debris captured by the magnetic field from the fluid. Thus, the debris monitor is preferably an intensity-based system so that the readings back at the transducer 22 will affected by losses and back scatter all along the optical path from the light source through the probe and back to the light detector. By preferably transmitting the light bidirectionally, each pair of light samples that traveled in opposite directions along the same optical path can be processed using difference-over-sum signal processing to normalize the signals. Thus intensity variations in the two signals other than those caused by the magnetic field are effectively canceled or normalized.

Figure 3:
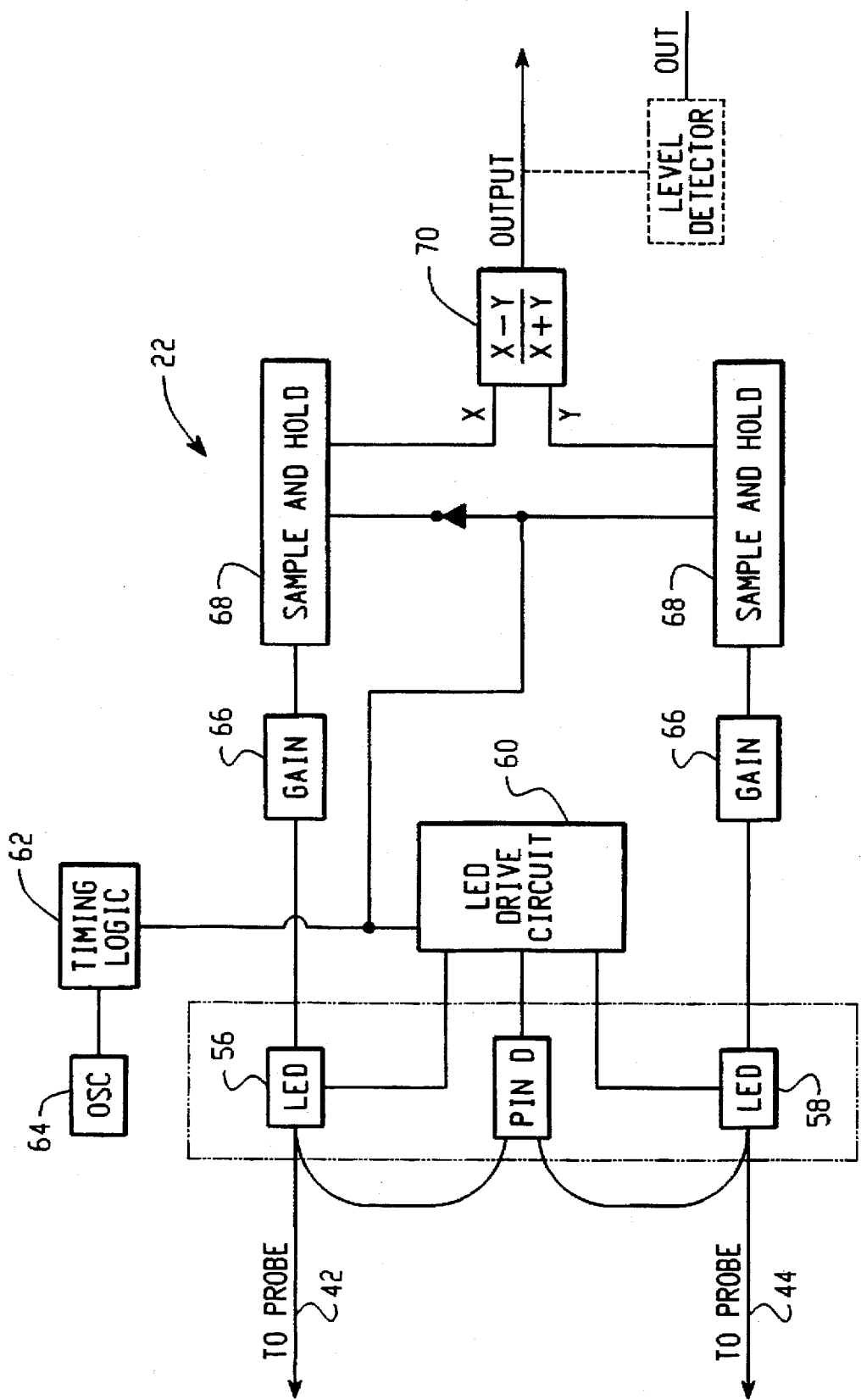
FIG. 3 is an electrical schematic of a preferred transducer circuit for use with the present invention.

Referring now to FIG. 3, a preferred circuit is shown for realizing the electro-optic transducer 22. This circuit can be realized with discreet components or as an integrated or hybrid circuit. The transducer 22 electronics can easily and conveniently be packaged within a small lightweight and hand-held unit. The transducer 22 includes a pair of light emitting diodes (LEDs) respectively optically coupled to the optic fibers 42, 44. Preferably, each LED functions as both a source and detector of light energy during the bidirectional operation of the debris monitor 10. Each LED 56,58 is operated under control of an LED drive circuit 60. A timing logic circuit 62 operates from a clock or oscillator 64 and controls when each LED is energized for emitting light into its respective fiber and alternatively used to detect light returning from the probe 14. As detectors, the LEDs can operate in the photocurrent or photovoltaic mode. Each LED produces an output signal that is amplified by a gain circuit 66 and these signals are input to respective sample and hold circuits 68 for further signal processing. A ratio circuit 70 can be used to compute the difference-over-sum ratio for signals produced by two light samples transmitted bidirectionally through the probe 14. Thus, when LED 56 is energized it launches light into the input fiber 42 which light travels through the probe 14 as described hereinbefore and returns via the output fiber 44. The returned light has an intensity that corresponds to the debris captured by the magnetic field of the plug 12. The second LED 44 serves at this time as a detector and produces an output signal proportional to the intensity of light incident thereon from the output fiber 44. The LED signal is then amplified and stored in the sample and hold circuit. The timing circuit 62 then reverses operation of the LEDs so that during the next sequence the first LED 56 now operates as a detector and the second LED operates as a light source. The first fiber 42 now serves as the output fiber and the second fiber 44 now serves as the input fiber to the probe 14. When the light returns from the probe it is similarly converted to an electrical signal that is sampled and held so that the ratio of the bidirectionally transmitted light samples can be computed.

As shown in FIG. 1, the probe assembly 14 can be fitted with an optional cover 80. Preferably the cover includes at least a portion that is magnetic so that the cover can be used not only to protect the probe assembly 14 but also can be used as a calibration device. The cover can establish a predetermined magnetic field for the probe so that the transducer 22 can be operated to verify the circuits are functioning properly and verify the integrity of the optical path and connections between the transducer 22 and the probe 14.

The invention thus provides a conveniently portable optical debris monitor that permits a real-time analysis of debris in a fluid. In the preferred embodiment the debris monitor uses a probe that is optically connected to an electro-optic transducer and can be mated to a plug in the fluid and operated without using electrical energy near the fluid. The probe operates with light and thus is insensitive to electromagnetic radiation. The debris monitor can easily be transported for use on different aircraft or other vehicles or machinery and provides a calibration cover for the probe.

While the invention has been shown and described with respect to specific embodiments thereof, this is for the purpose of illustration rather than limitation, and other variations and modifications of the specific embodiments herein shown and described will be apparent to those skilled in the art within the intended spirit and scope of the invention as set forth in the appended claims.

I claim:

1. A fluid debris monitor for detecting ferromagnetic debris in a fluid within a container, comprising magnetic plug means for producing a magnetic field in the fluid to capture debris, said magnetic field changing in relation to said captured debris; said magnetic plug means comprising a plug outer casing; transducer means for transmitting and receiving light energy; and optical probe means for detecting said captured debris by changing a characteristic of said light from said transducer means in relation to said magnetic field, said optical probe means being nonelectrically coupled to said transducer means and being entirely disposed in a probe outer casing that is selectively mated and unmated with said plug outer casing; wherein said magnetic field changes as debris is captured and said probe means comprises magneto-optic means for changing said light characteristic in response to said magnetic field changes and said transducer means converts light received from said probe means into an output that corresponds to said debris; and a removable cover means for protecting said probe means and for providing a calibration means for calibrating the debris monitor prior to mating said probe means and said plug means together.

2. A fluid debris monitor according to claim 1 wherein said transducer means and probe means are portable devices, said probe means being optically connectable to said transducer means by optic fiber means.

3. A fluid debris monitor according to claim 2 wherein said probe means is a hand-held device manually connectable to said plug means.

4. A fluid debris monitor according to claim 1 wherein said probe means comprises means for changing a polarization characteristic of said light, said polarization changes corresponding to said captured debris.

5. A fluid debris monitor according to claim 4 wherein said magnetic field changes as debris is captured, said probe means further comprising magneto-optic means for rotating said light polarization state in response to said magnetic field.

6. The fluid debris monitor of claim 1 wherein said cover means comprises a magnetic portion having a predetermined magnetic field for calibrating the debris monitor.

* * * * *